(12) United States Patent
Fry et al.

(10) Patent No.: US 10,495,548 B2
(45) Date of Patent: Dec. 3, 2019

(54) VACUUM PLATEN TISSUE PLANING APPARATUS

(71) Applicant: LifeCell Corporation, Branchburg, NJ (US)

(72) Inventors: Michael Alan Fry, Stillwater, MN (US); Jeremy Howe-Smith, Richboro, PA (US)

(73) Assignee: LifeCell Corporation, Madison, NJ (US)

( * ) Notice: Subject to any disclaimer, the term of this patent is extended or adjusted under 35 U.S.C. 154(b) by 3 days.

(21) Appl. No.: 15/418,975

(22) Filed: Jan. 30, 2017

(65) Prior Publication Data

US 2017/0212014 A1 Jul. 27, 2017

Related U.S. Application Data

(62) Division of application No. 14/577,494, filed on Dec. 19, 2014, now Pat. No. 9,594,004.
(Continued)

(51) Int. Cl.
*G01N 1/06* (2006.01)
*B26F 3/00* (2006.01)
(Continued)

(52) U.S. Cl.
CPC ............. *G01N 1/06* (2013.01); *A61B 17/322* (2013.01); *B26D 3/28* (2013.01); *B26D 7/018* (2013.01);
(Continued)

(58) Field of Classification Search
CPC ...... G01N 1/06; G01N 1/14; G01N 2001/061; G01N 2001/063; G01N 2001/065; Y10T 83/0453; Y10T 83/0591; Y10T 83/0605; Y10T 83/364; Y10T 83/748; Y10S 83/9155; B26F 3/004; B26F 1/3806; B26F 1/3813; B26F 1/384; B26D 3/28; B26D 7/018; B26D 7/20; A61B 17/322; A61B 17/3203; A61B 2017/00969; A61B 2017/306; A61B 2017/3225
See application file for complete search history.

(56) References Cited

U.S. PATENT DOCUMENTS 3,023,560 A 3/1962 Krahn
3,324,915 A 6/1967 Townsend
(Continued)

FOREIGN PATENT DOCUMENTS

CN 2125374 U 12/1992
DE 2411535 A1 9/1974
(Continued)

OTHER PUBLICATIONS

Form PCT/ISA/220 (Notification of Transmittal of the International Search Report (ISR)) and the Written Opinion of the International Searching Authority, or the Declaration, including the International Search Report (Form PCT/ISA/210).

*Primary Examiner* — Phong H Nguyen
(74) *Attorney, Agent, or Firm* — McCarter & English, LLP

(57) ABSTRACT

Devices and methods for processing animal or human tissue are provided. The devices may include a vacuum surface to secure the tissue in place and an apparatus for removing fat or other material from the tissue. The apparatus can include one or more blades and/or a fluid jet system.

10 Claims, 4 Drawing Sheets

Related U.S. Application Data

(60) Provisional application No. 61/925,884, filed on Jan. 10, 2014.

(51) Int. Cl.
   *B26D 3/28* (2006.01)
   *B26D 7/01* (2006.01)
   *B26D 7/20* (2006.01)
   *A61B 17/322* (2006.01)
   *A61B 17/3203* (2006.01)
   *A61B 17/00* (2006.01)
   *A61B 17/30* (2006.01)

(52) U.S. Cl.
   CPC ............ *B26D 7/20* (2013.01); *B26F 3/004* (2013.01); *A61B 17/3203* (2013.01); *A61B 2017/00969* (2013.01); *A61B 2017/306* (2013.01); *A61B 2017/3225* (2013.01); *Y10S 83/9155* (2013.01); *Y10T 83/0453* (2015.04); *Y10T 83/0591* (2015.04); *Y10T 83/0605* (2015.04); *Y10T 83/364* (2015.04); *Y10T 83/748* (2015.04)

(56) References Cited

U.S. PATENT DOCUMENTS

| | | | |
|---|---|---|---|
| 3,515,618 A | 6/1970 | Sidles | |
| 3,877,334 A * | 4/1975 | Gerber | B26D 7/018 83/169 |
| 4,020,528 A * | 5/1977 | Lindbladh | A22C 25/17 452/125 |
| 4,184,472 A * | 1/1980 | Benedicto | B26D 3/28 125/23.01 |
| 6,203,540 B1 | 3/2001 | Weber | |
| 6,253,653 B1 * | 7/2001 | Walter | G01N 1/06 83/703 |
| 6,685,657 B2 | 2/2004 | Jones | |
| 9,277,933 B1 | 3/2016 | Jessop et al. | |
| 2001/0029380 A1 | 10/2001 | Ysebaert | |
| 2002/0161385 A1 | 10/2002 | Wiener et al. | |
| 2003/0204199 A1 | 10/2003 | Novak et al. | |
| 2005/0113915 A1 * | 5/2005 | Marcaletti | A61F 2/105 623/15.12 |
| 2005/0222652 A1 | 10/2005 | Mori | |
| 2007/0219540 A1 | 9/2007 | Masotti et al. | |
| 2008/0110311 A1 * | 5/2008 | Stangherlin | B26F 1/3813 83/177 |
| 2009/0138027 A1 | 5/2009 | Lucas et al. | |
| 2009/0314314 A1 | 12/2009 | Klein et al. | |
| 2010/0022919 A1 | 1/2010 | Peterson | |
| 2010/0049178 A1 | 2/2010 | Deem et al. | |
| 2013/0025425 A1 * | 1/2013 | Knaupp | B26F 3/008 83/177 |
| 2014/0234895 A1 | 8/2014 | Morales | |

FOREIGN PATENT DOCUMENTS

| | | |
|---|---|---|
| DE | 9403937 U1 | 8/1994 |
| DE | 29722914 U1 | 2/1998 |
| WO | 01/32091 A2 | 5/2001 |
| WO | 2009140980 A1 | 11/2009 |

* cited by examiner

VACUUM PLATEN TISSUE PLANING APPARATUS

RELATED APPLICATION

This application is a division of U.S. patent application Ser. No. 14/577,494, filed Dec. 19, 2014, which claims the benefit of priority of U.S. Provisional Application Ser. No. 61/925,884, entitled "Vacuum Platen Tissue Planing Apparatus," filed Jan. 10, 2014, the content of each of the above applications being hereby incorporated by reference in its entirety.

BACKGROUND OF DISCLOSURE

The present disclosure relates to animal or human tissue processing, and more particularly, to devices and methods to remove a portion of material from animal or human tissue.

Various tissue-derived products are used to regenerate, repair, or otherwise treat diseased or damaged tissues and organs. Such products can include tissue grafts and/or processed tissues (e.g., acellular tissue matrices from skin, intestine, or other tissues, with or without cell seeding). Such products generally have properties determined by the tissue source (i.e., tissue type and animal from which it originated) and the processing parameters used to produce the tissue products.

Since tissue products are often used for surgical applications and/or tissue replacement or augmentation, the products should support tissue growth and regeneration, as desired for the selected implantation site. To accomplish these goals, the processes for obtaining and processing tissues are selected to avoid unacceptable damage or alteration to the tissues. In addition, it is desirable for the processing and collection methods to be as efficient as possible without unacceptably harming the tissues.

Collection of tissues used to produce tissue products generally includes separation of various tissue components from one another. For example, in order to collect portions of skin, such as dermis, for production of dermal tissue products, it is necessary to separate the dermis from subcutaneous tissues such as fat. Similarly, for other tissues, such as muscle, connective tissue, ligaments, tendons, or any other tissue, it is often necessary to separate the tissue from surrounding tissues before further processing.

Separation of tissues from one another can be time consuming and/or tedious. For example, separation of dermis from subcutaneous fat in large volumes can take significant effort and must be done without causing unacceptable alterations to the dermis.

Accordingly, the present disclosure provides methods and device for separating tissues from one another, including separating subcutaneous fat or other tissues from dermis.

SUMMARY

According to certain embodiments, a device for processing animal or human tissue is provided. The device can comprise a platen surface containing a group of holes, and a suction system configured to generate a negative pressure through the group of holes to secure a section of animal or human tissue to the platen surface. The device can further comprise at least one blade positioned proximate the platen surface to cut a portion of the section of animal or human tissue and a first carriage operably connected to the at least one blade and configured to carry the at least one blade across the platen surface to remove a portion of the animal or human tissue.

The platen surface can be attached to an adjustable frame assembly. The frame assembly can be positionable at an adjustable angle with respect to a supporting surface.

The at least one blade can comprise at least one reciprocating blade. The at least one blade can be attached to a support assembly configured to position the at least one blade at an adjustable angle with respect to the platen surface.

The device can further comprise at least one second blade. The at least one second blade can comprise at least one rotating blade. The at least one second blade can be positioned distal to the first blade with respect to the direction of movement of the first blade across the platen surface. The at least one second blade can comprise two or more blades in a spiral configuration. The device can comprise a second carriage to carry the at least one second blade across the platen surface.

The device can further comprise at least one fluid supply system. The at least one fluid supply system can provide high pressure fluid to the animal or human tissue.

The first carriage can be attached to a carriage assembly. The carriage assembly can comprise two rails positioned on opposite sides of the platen surface. The platen surface can be positioned at an angle such that the platen surface is not parallel to the ground. The platen surface can be positioned at an angle greater than 45° with respect to the ground.

According to other embodiments, a method for processing animal or human tissue is provided. The method can comprise selecting an animal or human tissue and placing the animal or human tissue on a platen surface containing a group of holes. The method can further comprise activating a suction system in fluid contact with the group of holes to secure the animal or human tissue to the platen surface and moving at least one blade proximate the platen surface to remove a portion of material from the animal or human tissue while maintaining the animal or human tissue in a stationary position on the platen surface.

Moving the at least one blade can comprise moving a carriage attached to the at least one blade across the platen surface. The method can further comprise adjusting the height of the at least one blade with respect to the platen surface to remove a selected depth of material from the animal or human tissue.

The method can further comprise moving at least one second blade across a surface of the tissue after moving the first blade proximate the platen surface to remove additional material from the tissue. The at least one second blade can comprise at least two blades having a spiral configuration. The method can further comprise activating at least one fluid supply system to remove additional material from the animal or human tissue. The method can further comprise adjusting an angle of the platen surface with respect to the ground.

The animal or human tissue can comprise an animal hide or human donated tissue. The animal hide can comprise porcine skin. The method comprises positioning a cutaneous portion of the skin against the platen surface, and wherein the method further comprises removing subcutaneous adipose, connective, and muscle tissue, from the skin.

According to other embodiments, the device can comprise a platen surface containing a group of holes, and a suction system configured to generate a negative pressure through the group of holes to secure a section of animal or human tissue to the platen surface. The device can further comprise at least one fluid supply system to provide high pressure fluid to the animal or human tissue to remove a portion of material from the tissue.

According to other embodiments, the method can comprise selecting an animal or human tissue and placing the animal or human tissue on a platen surface containing a group of holes. The method can further comprise activating a suction system in fluid contact with the group of holes to secure the animal or human tissue to the platen surface. In addition, the method can further comprise activating at least one fluid supply system proximate the platen surface to remove a portion of material from the animal or human tissue while maintaining the animal or human tissue in a stationary position on the platen surface.

According to certain embodiments, the device can comprise a platen surface containing a group of holes, means for securing a section of human or animal tissue to the platen surface, and means for removing a portion of the human or animal tissue while the tissue is secured to the platen surface.

DESCRIPTION OF EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless specifically stated otherwise. Furthermore, the use of the term "including", as well as other forms, such as "includes" and "included", is not limiting. Any range described herein will be understood to include the endpoints and all values between the endpints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirely for any purpose.

The present disclosure relates to animal or human tissue processing, and more particularly, to devices and methods for removal of a portion of material from animal or human tissue for surgical and/or medical applications. In order to use the tissue in surgical applications, it may be necessary to separate the tissue from surrounding materials or tissues to isolate desired portions of the tissue.

For example, suitable acellular tissue matrix products include acellular dermal materials such as ALLODERM® and STRATTICE™, which are human and porcine acellular dermal materials available from LIFECELL CORPORATION® (Branchburg, N.J.). In order to produce these acellular dermal materials, it is necessary to isolate the dermis from underlying tissues, including subcutaneous fat. Separation of such materials from the skin, however, can be time consuming. In addition, during the separation process it is important that the dermis remains intact and not damaged by the separation process (e.g., thru mechanical, chemical, or thermal damage). Accordingly, the present disclosure provides improved methods of separation animal or human tissues.

Figure 1:
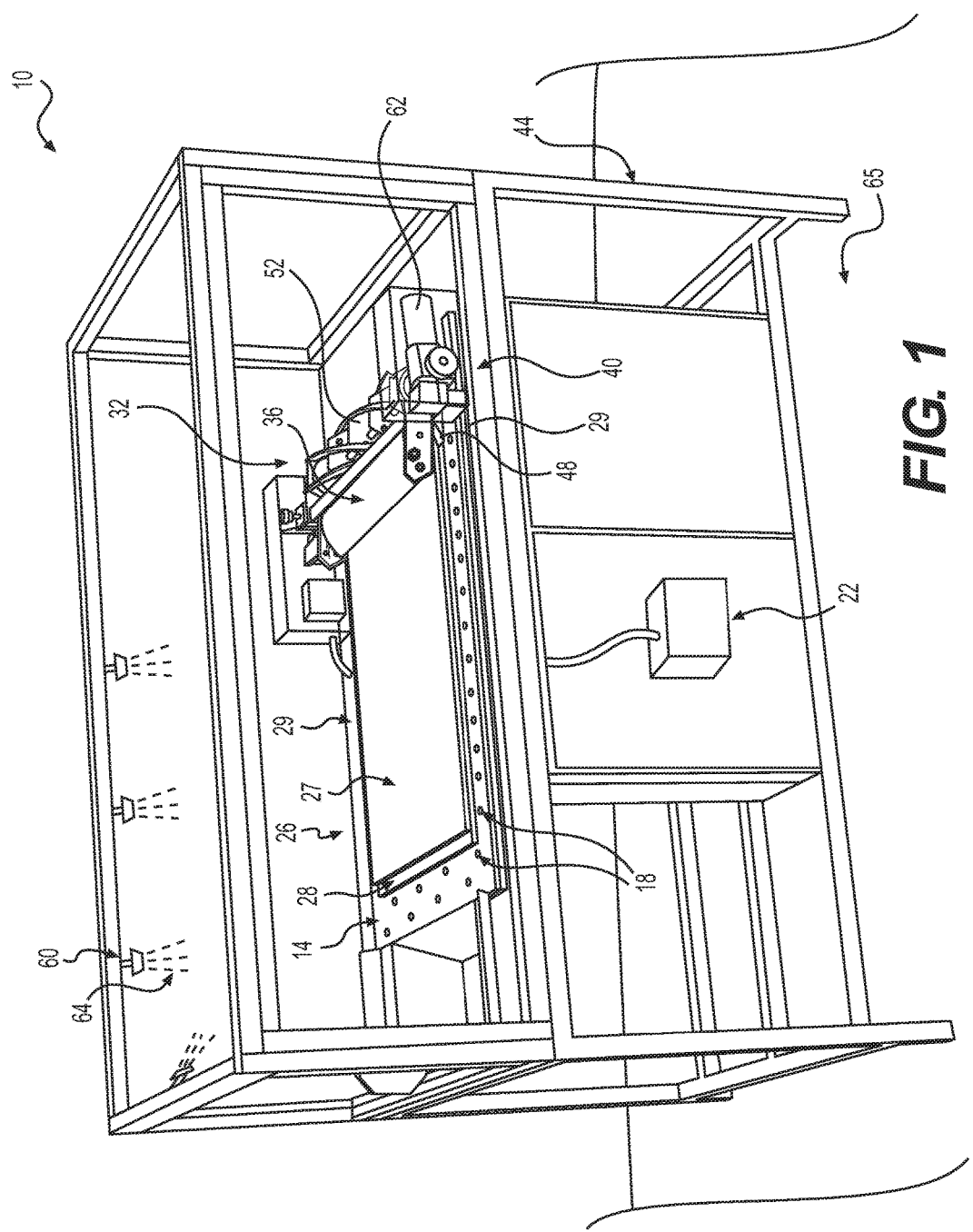
FIG. 1 illustrates a device for processing animal or human tissue, according to certain embodiments.

FIG. 1 illustrates a device 10 for processing animal or human tissue, according to certain embodiments. As shown, the device 10 can comprise a platen surface 14 containing a group of holes 18 and a suction system 22 configured to generate a negative pressure through the group of holes 18 to secure a section of animal or human tissue 26 to the platen surface 14.

The device 10 can further comprise at least one blade 32 positioned proximate the platen surface 14 to cut a portion 36 of the section of animal or human tissue 26 and a first carriage 40 operably connected to the at least one blade 32 and configured to carry the at least one blade 32 across the platen surface 14 to remove a portion 36 of the animal or human tissue 26.

The platen surface 14 can be constructed from a variety of different materials. Generally, the platen surface 14 will be substantially or completely flat and constructed from a rigid material such as stainless steel, a rigid plastic, or other similar material. As such, when the section of animal or human tissue 26 is placed on the platen surface 14, the section of animal or human tissue 26 will lie flat, and the distance of the blade 32 from the platen surface 14 will be constant across the area of the section of animal or human tissue 26, thereby providing a constant frame of reference for cutting the section of animal or human tissue 26.

As noted, the platen surface 14 can comprise a group of holes 18 and a suction system 22 configured to generate a negative pressure through the group of holes 18 to secure a section of animal or human tissue 26 to the platen surface 14. As such, the section of animal or human tissue 26 can be held securely in place while the section of animal or human tissue 26 is cut by the blade 32, which can move across the platen surface 14. That is to say, the tissue does not move, but is held in a static position, thereby ensuring a stable position and providing a more consistent cut of the tissue 26 than systems in which the tissue 26 may be moved relative to the blade, e.g., along a conveyor blade, as may be used in food or other non-medical industries.

The suction system 22 can include any mechanized system for generating a negative pressure through the group of holes 18. For example, the suction system 22 can include a standard vacuum pump, including a vacuum configured for generally cleaning purposes. In general, the vacuum should be selected to generate a sufficient negative pressure to secure the section of animal or human tissue 26 on the platen surface 14 during cutting of the animal or human tissue 26.

The platen surface 14 can include a variety of shapes and sizes. For example, generally, the platen surface 14 will be sized and shaped to allow efficient processing of the selected animal or human tissue. For example, as discussed further below, the animal or human tissue 26 can include an animal hide or human donor tissue, including skin and attached subcutaneous tissues. In some embodiments, the animal or human tissue comprises porcine skin, and the platen surface includes a rectangular shape sized for processing typical porcine hides.

As noted, the device 10 can include at least one blade 32. In certain embodiments, the device 10 includes multiple blades. For example, in some embodiments, the at least one blade 32 includes a first blade 48 and a second blade 52. As shown, the first blade 48 can be configured to move adjacent to and through a section of animal or human tissue 26 to separate layers 27, 28 of the tissue. Subsequently, the second blade 52 can follow the at least one first blade 48 to remove additional tissue from the section of animal or human tissue 26.

Figure 3:
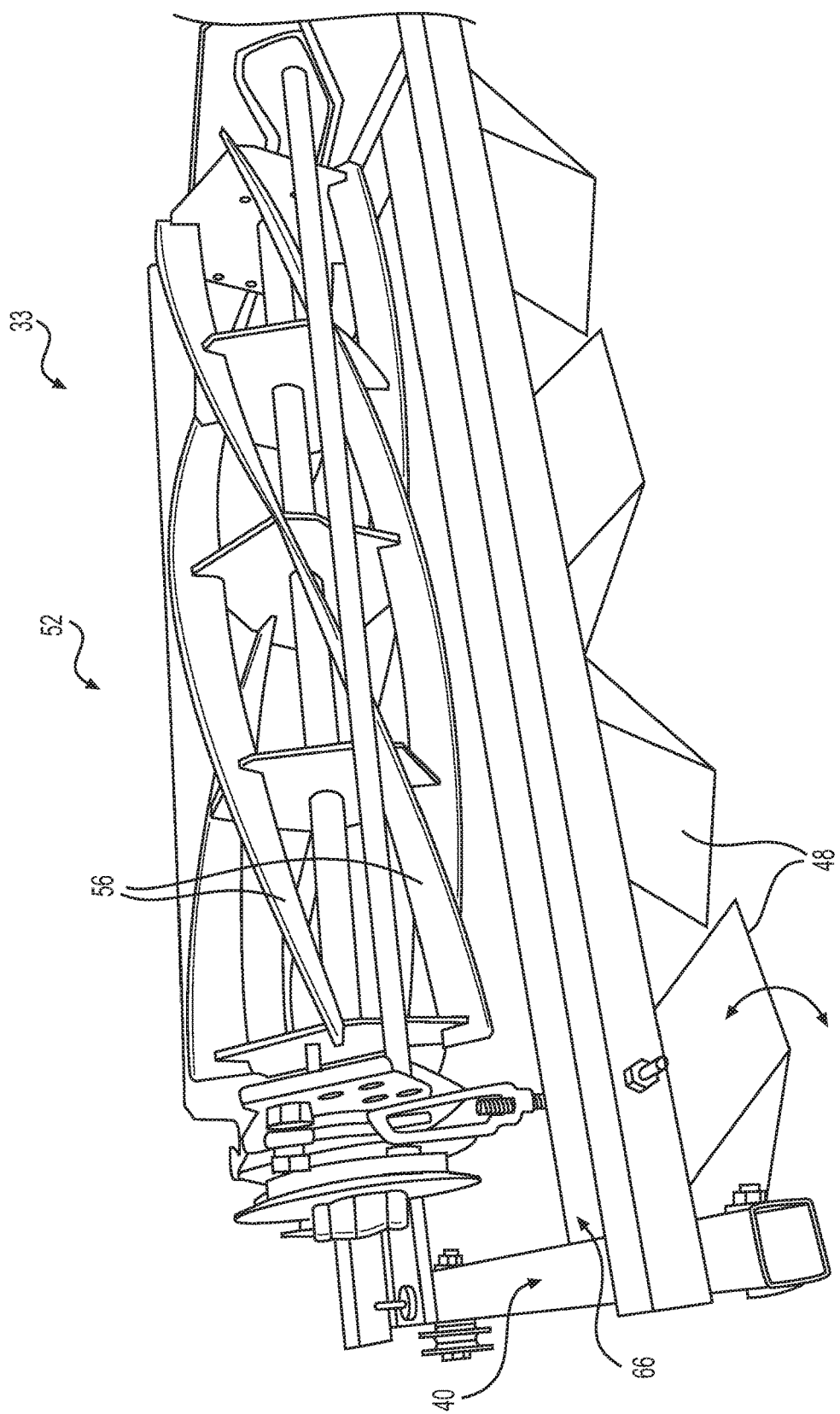
FIG. 3 illustrates a blade assembly suitable for removal of fat from animal skin using devices of the present disclosure, according to certain embodiments.

The at least one blade 32 can include a variety of different blade types suitable for cutting animal or human tissue. For example, FIG. 3 illustrates a blade assembly 33 suitable for removal of fat from animal skin using devices of the present disclosure, according to certain embodiments. in some embodiments. As shown, the blade assembly 33 include at least one first blade 48 and at least one second blade 52. In addition, the blades 48, and 52 are attached to at least one carriage 40.

The at least one first blade 48 can comprise a number of blade types. For example, as shown, the at least one first blade 48 includes one or more reciprocating blades configured to cut the section of animal or human tissue 26 along a single plane. In addition, the at least one first blade 48 may be attached to an adjustment system 66, which may allow adjustment of an angle and/or height of a reciprocating blade.

As noted, the device 10 can further comprise at least one second blade 52. In certain embodiments, the at least one second blade 52 can comprise at least one rotating blade. In some embodiments, the at least one second blade 52 can comprise two or more blades 56 in a spiral configuration. The blades 48, 52 can be operatively connected to a power source 62. For example, suitable power sources can include gas or electric motors configured to drive reciprocation or rotating blades.

As discussed above, the section of animal or human tissue 26 can be secured to the platen surface and the blades 48, 52 can be moved relative to the platen surface to allow removal of a portion of the tissue. In some embodiments, the blades are attached to one or more carriages 40 configured to move along the platen surface. For example, the carriages 40 can include a motorized or manually driven carriage 40 configured to slide or roll along two rails 29 positioned on opposite sides of the platen surface 14.

Figure 2:
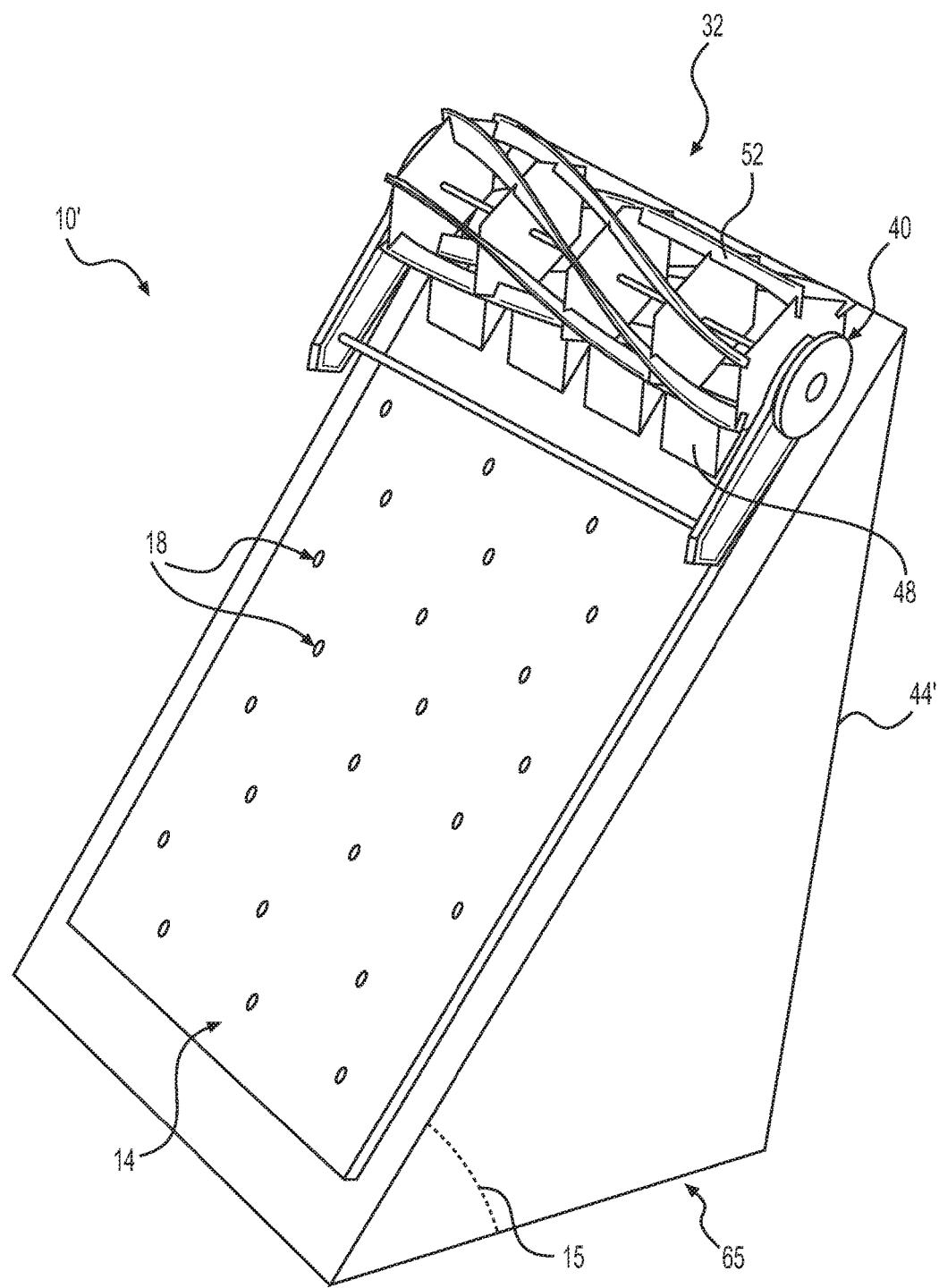
FIG. 2 illustrates a device for processing animal or human tissue, according to certain embodiments.

In some embodiments, the platen surface 14 can be attached to an adjustable frame assembly 44, and the frame assembly 44 can be positionable at an adjustable angle with respect to a supporting surface 65. FIG. 2 illustrates a device 10' for processing animal or human tissue, according to certain embodiments. The platen surface 14 can be positioned at an angle 15 such that the platen surface 14 is not parallel to the ground 65. As shown, the animal or human tissue 26 is held in place, and the blades 48, 52 move vertically from top to bottom while cutting the tissue. As such, cut tissue can be more easily removed from the blade path by force of gravity. In certain embodiments, the platen surface can be positioned at an angle greater than 45° with respect to the ground.

In some embodiments, the device can further comprise at least one fluid supply system 60 to provide high pressure fluid 64 to the animal or human tissue 26 to remove a portion of tissue in conjunction with the blades 48, 52. The fluid supply system 60 should be positioned in a way to direct the fluid stream 64 to remove additional material from the animal or human tissue 26.

Figure 4:
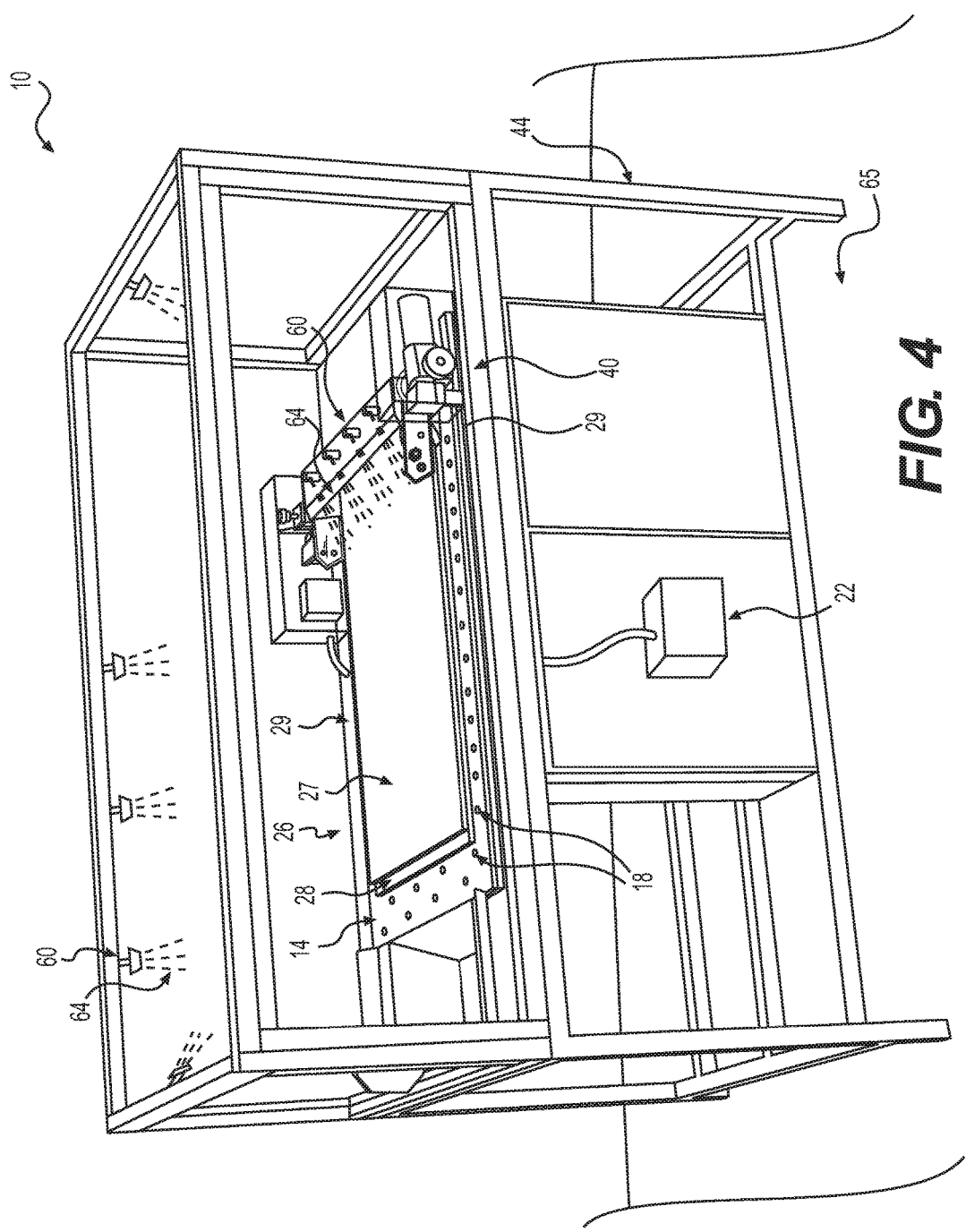
FIG. 4 illustrates a device for processing animal or human tissue, according to certain embodiments.

As noted above, the fluid supply system 60 can be used in conjunction with the blades 48, 52 to remove material from animal or human tissue 26, or it can be used alone in order to remove material from animal or human tissue 26, e.g. FIG. 4.

FIG. 4 illustrates a device 10 for processing animal or human tissue, according to certain embodiments. The at least one fluid supply system 60 is configured to provide high pressure fluid stream 64 to the animal or human tissue 26 to remove material from the animal or human tissue 26. As discussed above, the fluid supply system 60 can be positioned in a way to direct the fluid stream 64 to remove material, including subcutaneous fat, from the animal or human tissue 26.

In some embodiments, the fluid supply system 60 can be attached to the frame assembly 44 and provide fluid streams 64 towards the animal or human tissue 26. In addition, the fluid supply system 60 can be connected to the first carriage 40 so that the system 60 can be moved along the platen surface 14 to remove material from animal or human tissue 26 by producing high pressure fluid stream 64. The fluid supply system 60 in any of the foregoing embodiments can include several fluid supply systems 60. The pressure of the fluid stream 64 can be any suitable pressure selected not to damage the animal or human tissue 26 while contacting the surface of animal or human tissue 26. The fluid supply system 60 may be positioned at any height relative to the animal or human tissue 26. The high pressure fluid stream 64 provided by the fluid supply system 60 can be any kind of fluid, e.g. water, suitable for removing desired material from the tissue.

The invention claimed is:

1. A device for processing animal or human tissue comprising:
   a platen surface containing a group of holes;
   a suction system configured to generate a negative pressure through the group of holes to secure a first side of a multi-layer section of animal or human tissue flat against the platen surface;
   at least one fluid supply system, wherein the at least one fluid supply system provides high pressure fluid to the animal or human tissue to remove at least a top layer of material from a second side opposite the first side of the tissue; and
   at least one first blade positioned proximate the platen surface to cut the at least a top layer of material from the second side of the tissue in conjunction with the at least one fluid supply system.

2. The device of claim 1, wherein the platen surface is attached to an adjustable frame assembly.

3. The device of claim 2, wherein the frame assembly is positionable at an adjustable angle with respect to a supporting surface.

4. The device of claim 1, further comprising a first carriage to carry the at least one fluid supply system along the platen surface.

5. The device of claim 4, wherein the first carriage is attached to a carriage assembly.

6. The device of claim 5, wherein the carriage assembly comprises two rails positioned on opposite sides of the platen surface.

7. The device of claim 1, wherein the platen surface is positioned at an angle such that the platen surface is not parallel to the ground.

8. The device of claim 7, wherein the platen surface is positioned at an angle greater than 45° with respect to the ground.

9. The device of claim 1, further comprising a carriage operably connected to the at least one first blade and configured to carry the at least one first blade along the platen surface to remove the at least a top layer of material from the second side of the tissue in conjunction with the at least one fluid supply system.

10. The device of claim 1, wherein the fluid supply system is a first fluid supply system and the device further comprises a second fluid supply system.

\* \* \* \* \*